US005747345A

United States Patent [19]

Weber, II et al.

[11] Patent Number: 5,747,345
[45] Date of Patent: May 5, 1998

[54] CALCIUM SPECIFIC DIAZA-18-CROWN-6-ETHER CHROMOIONOPHORES

[75] Inventors: Wayne Woodrow Weber, II, Honeoye Falls; Calvin Roman Messing, Spencerport; Margaret Elizabeth Logan, Rochester, all of N.Y.

[73] Assignee: Johnson & Johnson Clinical Diagnostics, Inc., Rochester, N.Y.

[21] Appl. No.: 698,316

[22] Filed: Aug. 15, 1996

[51] Int. Cl.$^6$ ................................................. G01N 33/20
[52] U.S. Cl. ........................... 436/74; 422/56; 422/57; 422/58; 436/73; 436/79; 436/164; 436/166; 436/169; 534/670; 534/751; 534/770; 534/797; 534/816; 534/831
[58] Field of Search .................. 260/330, 6; 534/649, 534/586, 651, 770, 884, 670, 751, 797, 816, 831; 436/73, 74, 79, 164, 166, 169; 422/56–58

[56] References Cited

U.S. PATENT DOCUMENTS

| | | | |
|---|---|---|---|
| 4,367,072 | 1/1983 | Vogtle et al. | 436/501 |
| 4,597,903 | 7/1986 | Gokel et al. | 260/330.6 |
| 4,603,209 | 7/1986 | Tsien et al. | 548/236 |
| 4,649,123 | 3/1987 | Charlton et al. | 436/79 |
| 4,795,712 | 1/1989 | Toner et al. | 436/74 |
| 4,871,679 | 10/1989 | Tanaka et al. | 436/79 |
| 4,966,784 | 10/1990 | Tanaka et al. | 427/2 |
| 5,245,021 | 9/1993 | Engebrecht et al. | 534/649 |
| 5,310,888 | 5/1994 | Bloczynski et al. | 436/79 X |
| 5,391,483 | 2/1995 | Danielson et al. | 435/28 |

OTHER PUBLICATIONS

T. Yamashita et al., *Bull. Chem. Soc. Jpn.* 1980, 53, 1550–1554.
H. NiShida et al., *Mikrochim. Acta* 1981, 1, 281–287.
H. NiShida et al., *Chem. Lett.*, 1982, 1853–1854.
H. Lu et al., *Huaxue Xuebao* 1987, 45, 893–899.
Y. Katayama et al., *Anal. Chim. Acta* 1988, 204, 113–125.
T.L. Blair et al., *Anal. Lett.* 1992, 25, 1823–1834.
H. Kido et al. *Bull. Chem. Soc. Jpn.* 1993, 66, 432–436.
Analytical Letters, vol. 10 (13), 1115–1122 (1977), (Takagi, Nakamura, And Ueno) A Novel Colorimetric Reagent For Potassium Based On Crown Ether Complex Formation[1].
Bunseki Kagaku vol. 32, pp. E293–E300. 1983, The Japan Society For Analytical Chemistry, 1983.
Crown Ether–Based Extraction Photometric Reagents For Calcium (Shiga, Nishida, Nakamura, Takagi And Ueno).

*Primary Examiner*—Arlen Soderquist
*Attorney, Agent, or Firm*—Kenneth J. Dow

[57] ABSTRACT

Diaza-18-crown-6 compounds of the formula I:

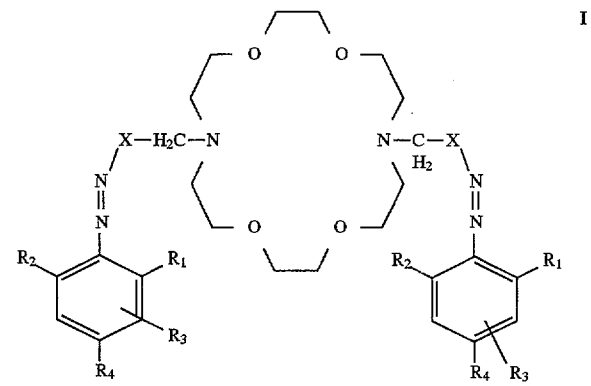

wherein X is a phenol, naphthol or quinolinol moiety selected from those of the formulae:

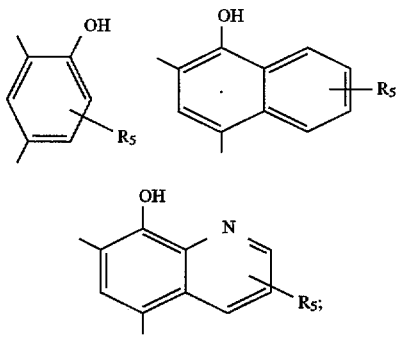

$R_1$, $R_2$, $R_3$, $R_4$ and $R_5$ are independently selected from hydrogen, halo, cyano, nitro, ($C_1$–$C_6$) alkyl, ($C_2$–$C_8$) acyl, acetamido, mercapto, alkyl or arylsulfonyl, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, alkyl or arylsulfonyl and trifluoromethyl; provided that when $R_1$, $R_2$, $R_3$ and $R_5$ are hydrogen and X is phenol, $R_4$ is not nitro; and provided that when X is phenol and $R_5$ is hydrogen, $R_1$ (or $R_2$) and $R_4$ are not both nitro. Compounds of the above formula are useful as chromoionophores for the detection of calcium ions in solution or dry assays, but are of particular advantage when used in dry, thin-film multilayer analytical elements.

14 Claims, 2 Drawing Sheets

CALCIUM SPECIFIC DIAZA-18-CROWN-6-ETHER CHROMOIONOPHORES

FIELD OF THE INVENTION

The present invention relates to the field of clinical chemistry, particularly novel compounds for use in calcium assays and to analytical compositions, elements and methods of using the same.

BACKGROUND OF THE INVENTION

Analytical assays for determination of calcium content have application in a variety of fields. One important application is in the field of clinical chemistry where the measurement of calcium levels in biological fluids such as serum can be used for diagnostic purposes as an indication of certain pathological conditions. For example, elevated serum calcium can be an indication of disorders of the parathyroid and thyroid glands, in sarcoidosis and in several metastasizing carcinomas. Hypercalcemia is also connected with osteoporosis, osteoplastic carcinomas, acute pancreatitis and acidosis.

Calcium levels can be determined quantitatively using a number of analytical methods. In general, direct colorimetric procedures involving the complexation of a dye with calcium ions are preferred over other, more complex methods. In the colorimetric assay, contact of the calcium ion with a chromoionophore causes a shift in the absorbance spectrum of the chromophore which can be measured quantitatively. One such dye that is commonly used for such purposes is known as Arsenazo III (2,2'-(1,8-dihydroxy-3,6-disulfonaphthylene-2,7-bisazo)bisbenzenearsonic acid (See Anal.Chim.Acta, 71, 375 (1974)). While this dye works quite well, its use on a large scale is limited due to environmental concerns.

The use of dry thin-film multilayer analytical elements such as those described in U.S. Pat. No. 3,992,158 to Przybylowicz et al. and U.S. Pat. No. 4,258,001 to Pierce et al. are now generally used for conducting assays in the field of clinical chemistry. These elements generally have a porous spreading layer and a reagent layer on a nonporous support. One such element has been designed for the determination of calcium ions and is marketed as the VITROS Clinical Chemistry Slide by Johnson & Johnson Clinical Diagnostics, Inc. (Rochester, N.Y.). This element utilizes the aforementioned Arsenazo dye which selectively complexes with calcium to provide a detectable change in color. However, as mentioned, environmental concerns have prompted a desire for new calcium complexing compounds that can be incorporated into such dry analytical elements.

Crown ether compounds, including diaza-18-crown-6 compounds, have been known for some time for their cation complexing properties. The introduction into a crown ether of a chromophore which changes color upon complexation of a cation with the crown ether has been reported. See e.g. Anal. Letters, 10(13), 1115–1122 (1977). M. Shiga et al, Bunseki Kagaku, 32(9), E293–E300, (1983) discloses certain N,N-disubstituted-diaza-18-crown-6 compounds having 2-hydroxy-5-(nitrophenylazo)-benzyl chromophore substituents for use as chromoionophores in solution assays for calcium. However, these compounds cannot be used effectively in dry slide chromogenic assay elements due to the difficulty in incorporating them into coating solutions or dispersions for application in thin-film chromoionophore coatings. Furthermore, photometers in commercial analyzers are typically filtered to read at or above 600 nm to avoid interference from bilirubin and other sample or assay components which absorb below 600 nm. The dinitrophenylazo compound of Shiga et al has an absorption peak below the desired read window, i.e. its λmax is about 575 nm.

SUMMARY OF THE INVENTION

The invention provides new diaza-18-crown-6 compounds of the formula I:

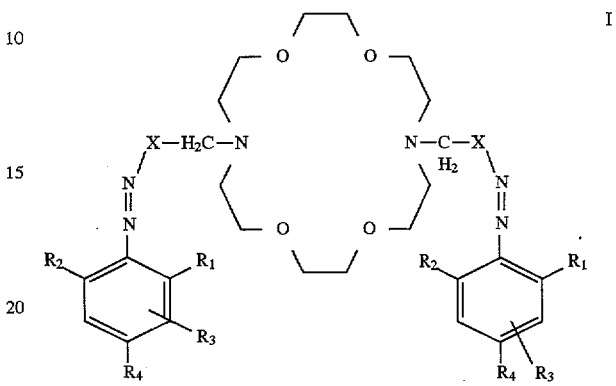

wherein X is phenol, naphthol or quinolinol moiety selected from those of the formulae:

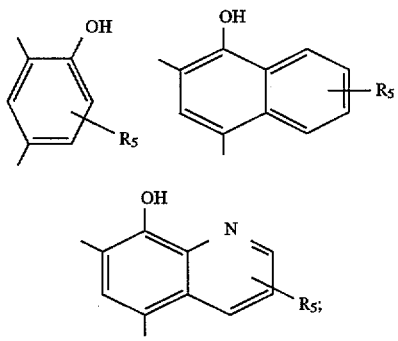

$R_1$, $R_2$, $R_3$, $R_4$ and $R_5$ are independently selected from hydrogen, halo cyano, nitro, ($C_1$–$C_6$) alkyl, ($C_2$–$C_8$) acyl, acetamido, mercapto, alkyl or arylsulfonyl, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, alkyl or arylsulfonyl and trifluoromethyl; provided that when $R_1$, $R_2$, $R_3$ and $R_5$ are hydrogen and X is phenol, $R_4$ is not nitro; and provided that when X is phenol and $R_5$ is hydrogen, $R_1$ (or $R_2$) and $R_4$ are not both nitro.

Compounds of the above formula are useful as chromoionophores for the detection of calcium ions in solution or dry assays, but are of particular advantage when used in dry, thin-film multilayer analytical elements because they can be readily dispersed in coupler solvents and uniformly coated as a thin-film to provide dry slide analytical elements for calcium. The compounds of the above formula having electron withdrawing substituents in the $R_1$, $R_2$ or $R_4$ positions can be read at an absorbance spectrum at or above 600 nm, which is of particular benefit in those assay systems where there are interferences at the lower wavelengths. Preferably, for use in thin film assay systems, particularly the aforementioned VITROS dry assay system, compounds of the present invention which absorb at a wavelength greater than 560 nm, preferably greater than 580 nm, when complexed with calcium ions, are preferred.

Accordingly, the invention also provides an analytical element for the determination of calcium ions comprising an absorbent carrier material containing the chromoionophore compound described above.

Further, a method for quantitative determination of calcium ions is provided which comprises:

(a) contacting a liquid sample suspected of containing calcium ions with the chromoionophore compound described above; and (b) determining calorimetrically the quantitative presence of calcium in the sample by measuring the optical density change resulting from the complexation of calcium ions with the compound.

DETAILED DESCRIPTION

Figure 1:
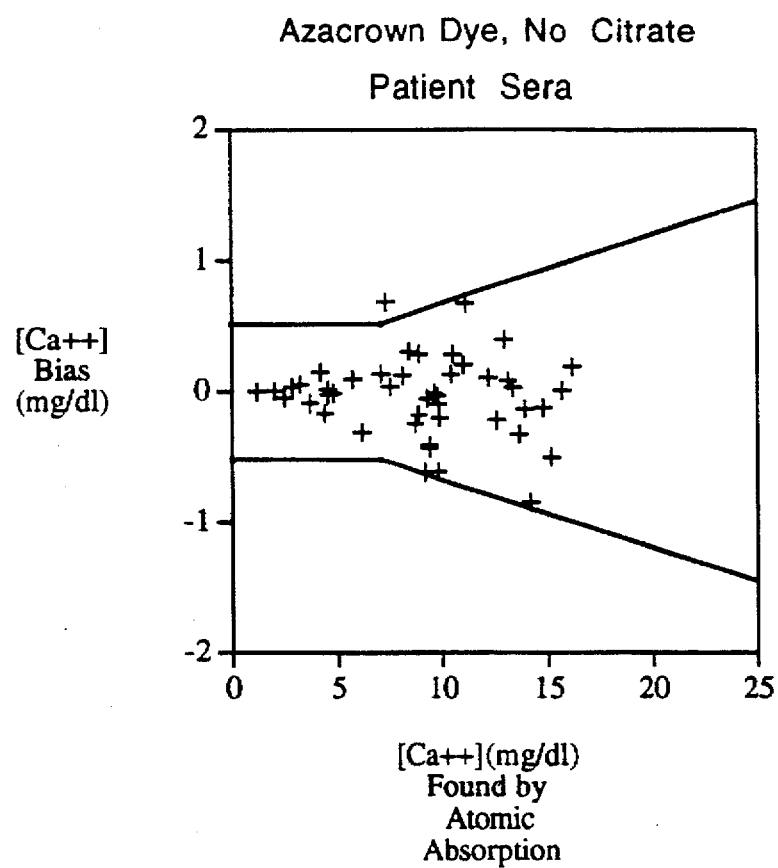
FIG. 1 is a graph of the calcium levels measured in serum samples using the analytical elements of the present invention without added citrate and showing the bias from the predicted calcium levels.

Relative to the above description, compounds of Formula I which are preferred for thin-film multilayer dry slide analytical elements for use with analyzers which operate at wavelengths of 580 nm or greater are those compounds wherein X is phenol, $R_1$ and $R_2$ are independently selected from hydrogen and an electron withdrawing group selected from halo, cyano, nitro, acyl of 2 to 8 carbon atoms, alkyl or arylsulfonyl, and triflouromethyl, provided that at least one of $R_1$ and $R_2$ is an electron withdrawing group; $R_3$ is selected from hydrogen, halo, cyano, nitro, ($C_1$–$C_6$) alkyl, ($C_2$–$C_8$) acyl, acetamido, mercapto, alkyl or arylsulfonyl, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, alkyl or arylsulfonyl, and trifluoromethyl; $R_4$ is nitro and $R_5$ is hydrogen.

Particularly preferred for such purposes are compounds wherein X is phenol, $R_1$ and $R_2$ are independently selected from hydrogen and an electron withdrawing group selected from halo, cyano, nitro, acyl of 2 to 8 carbon atoms, alkyl or arylsulfonyl, and triflouromethyl, provided that at least one of $R_1$ and $R_2$ is an electron withdrawing group; $R_3$ is ($C_1$–$C_6$) alkyl; $R_4$ is nitro and $R_5$ is hydrogen, provided that when one of $R_1$ or $R_2$ is trifluoromethyl and the other is hydrogen, $R_3$ may also be hydrogen.

Compounds of Formula I which are most preferred for such purposes are those in which X is phenol, $R_1$ is trifluoromethyl; $R_2$ and $R_3$ are hydrogen and $R_4$ is nitro. In such a compound, the trifluoromethyl group serves as both the hydrophobic group to facilitate dispersability in coupler solvents and as the electron withdrawing group to provide high (peak) absorption at or above 580 nm.

The compounds of Formula I that are the subject of this invention may be prepared from readily available starting materials in accordance with the following general procedures outlined in Schemes I–II:

SCHEME I

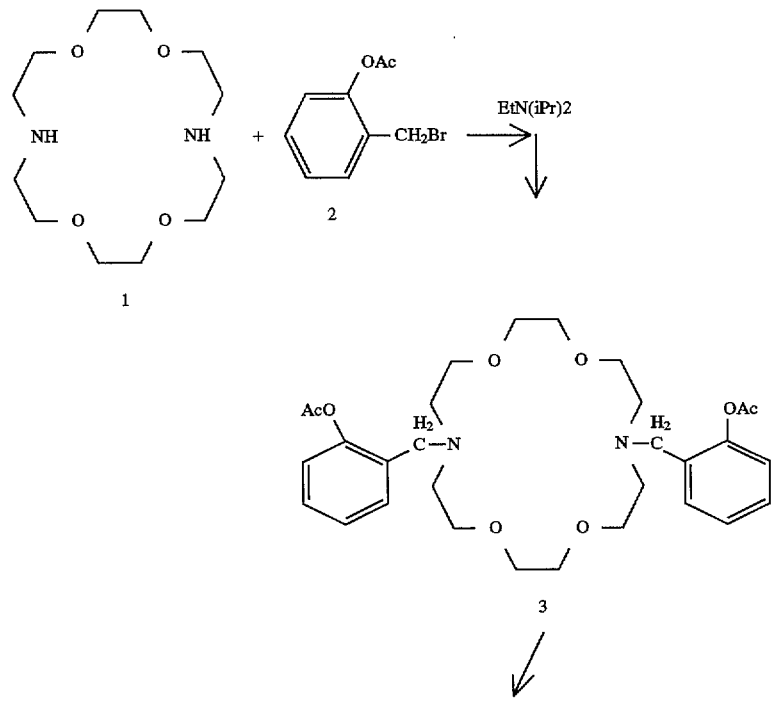

-continued
SCHEME I

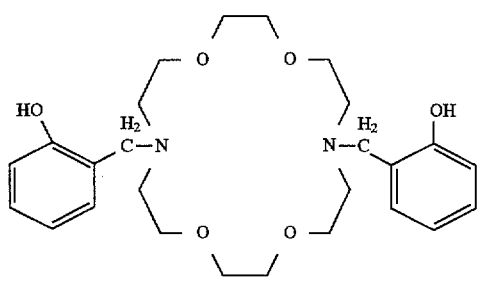

4

In accordance with Scheme I, a 4,13-diaza-18-crown-6 compound of formula 1 is reacted with 2-acetoxybenzyl bromide in the presence of N,N-diisopropyl-N-ethylamine to yield the benzyl-acetate compound of formula 3. Treatment with a weak acid such as acetic acid in $H_2O$ gives the 2-hydroxybenzyl intermediate of Formula 4. To prepare the compounds where X is a naphthol or quinoline moiety, an appropriately substituted naphthyl or quinoline compound may be substituted for the phenyl compound of Formula 2 above.

SCHEME 2

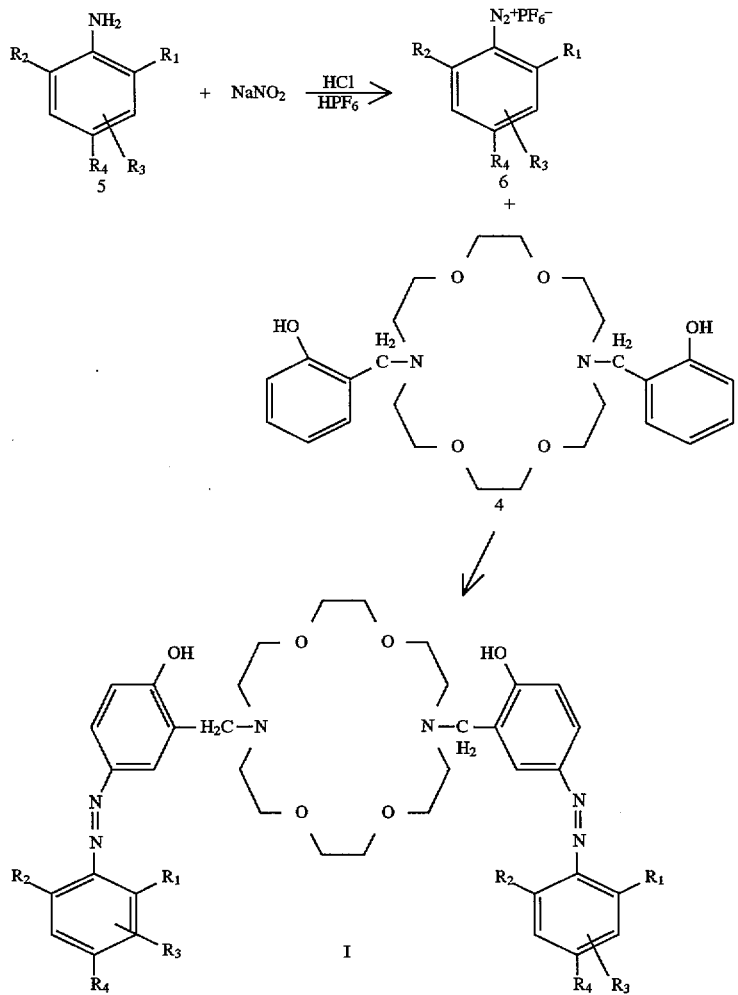

In accordance with Scheme 2, a substituted aniline compound of general formula 5 is first reacted with sodium nitrite in hydrochloric acid and then treated with hexafluorophosphoric acid to produce the phenyldiazonium hexafluorophosphate intermediate 6. Two equivalents of intermediate 6 are then reacted with one equivalent of the hydroxybenzyl-diaza-18-crown-6 intermediate 4 from Scheme I in a suitable solvent to yield the final compound of Formula I. The appropriately substituted naphthol or quinolinol compound may of course be substituted for the hydroxybenzyl intermediate 4.

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

In accordance with the present invention there is provided novel chromoionophore compositions that can be used for the qualitative or quantitative determination of calcium ions in aqueous liquids. Advantageously, the compositions can be used in analytical methods for the determination of calcium levels in biological fluids such as whole blood, plasma, sera, lymph, bile, urine, spinal fluid, sputum, perspiration, stool secretions and the like. Fluid preparations of human or animal tissue such as skeletal muscle, heart, kidney, lung, brain, bone marrow, skin and the like can also be assayed for calcium levels in accordance with the present invention.

When used for the above purposes, the compounds of the present invention exhibit a number of advantages over the compositions of the prior art. Specifically, the dye produced by the chromoionophore compounds of the present invention, on complexation with calcium ions, can be measured on peak for best performance. Further, a wider range of calcium concentrations can be measured without dilution and, as mentioned, the compounds can be readily dispersed in coupler solvents and uniformly coated as a thin film to provide dry slide analytical elements. Finally, the compounds are easily synthesized and do not require any toxic heavy metals.

The compounds can be used in solution assays or in dry analytical elements. When used in solution assays, the compounds are dissolved in an appropriate buffer solution to a pH of about 6 to 9. The aqueous composition for solution assay usually contains about 50, and preferably about 100, to about 300, μmolar calcium complexing compound of the invention. The assay is carried out by admixing the chromoionophore compound of the invention with a sample of fluid suspected of containing ionic calcium for a short time. The concentration of calcium ion is then determined by measuring the optical density change, (i.e., the shift in spectral absorption) caused by the complexation of the compound with calcium ions at the appropriate wavelength using suitable calorimetric detection equipment. Advantageously, for use in thin-film embodiments in particular, the compounds can be selected to absorb at a wavelength at or about 600 nm upon complexation.

The chromoionophore compounds of the invention can also be utilized in dry analytical elements. The simplest element can be composed of an absorbent carrier material, for example, a thin sheet of a self-supporting absorbent or bibulous material, such as filter paper or strips, which contain the complexing compound of this invention. The element can be divided into two or more discrete zones with different reagents incorporated into different zones of the carrier material. Such elements are known in the art as test strips, diagnostic elements, dip sticks, diagnostic agents and the like.

The chromoionophore compounds of the present invention are particularly useful when employed in dry analytical elements. In such elements, the compounds are generally incorporated into, or coated upon, a suitable carrier material. Alternatively, the compound can be added to the element during an assay. The dry analytical element can be multilayered and can be made by techniques well known in the dry analytical element art. For example, such elements and methods for their production are disclosed in U. S. Pat. No. 4,357,363. In one embodiment, the element includes a spreading layer, a subbing layer, a gelatin buffer layer and a reagent layer containing the compound and buffer. All of the foregoing layers are coated upon a support.

Other embodiments are also known, for example, one embodiment includes a combined reagent/spreading layer along with a subbing layer having at least two distinct zones. In this element buffer is incorporated into the spreading layer by means of either coating on the complete element or ball milling buffer into the spreading layer prior to coating.

In all embodiments the layers are generally in fluid contact with each other, meaning that fluids can be transported between superposed regions of adjacent zones. In other words, when the element is contacted with an aqueous fluid, all diffusable reagents of the analytical composition of this invention and the diffusable constituents of the aqueous fluid are mixed to form a homogeneous blend.

Useful spreading layers can be prepared using fibrous materials, either mixed with a suitable binder material or woven into a fabric, as described in U.S. Pat. No. 4,292,272 to Katajima et al., polymeric compositions or particulate materials, for example a blush polymer as disclosed in U.S. Pat. No. 3,992,158, beads bound together with or without binding adhesives, as described in U.S. Pat. No. 4,258,001 to Pierce et al. Particularly useful spreading layers comprise barium sulphate or titanium dioxide. Since the sample is generally applied directly to the spreading layer, it is desirable that the spreading layer be isotropically porous, meaning that the porosity is the same in each direction in the layer as caused by interconnected spaces or pores between particle, fibers or polymeric strands.

The elements can also contain one or more other addenda commonly put in the elements for various manufacturing and operational advantages. Such addenda include surfactants, buffers, bacteriostats, solvents, hardeners and other materials known in the art.

The layers can be coated on transparent (i.e. radiation transmissive) supports such as poly(ethylene terephthalate). Other supports are well known in the art.

In the elements, the chromoionophore compound of this invention is generally present in one or more zones in a coverage of at least about 0.10, and preferably from about 0.10 to about 1.5 g/m$^2$. Other reagents and materials are present in coverages within the skill of a worker in the art.

The elements of the invention can be configured in a variety of forms, including elongated tapes of any desired width, sheets, slides or chips.

The elements can be used in manual or automated assay techniques. In general, in using the dry elements, calcium ion determination is made by taking the element from a supply roll, chip packet or other source and physically contacting it with the sample (for example from 1 μL to up to 200 ml) of the fluid to be tested so that the sample and reagents within the element become mixed. Such contact can be accomplished by any suitable manner, for example, by dipping or immersing the element into the sample or, preferably, by spotting the element by hand or machine with a drop of the sample with a suitable dispensing means.

After sample application, the element is incubated at a temperature within a range of 15° to 50° C., preferably 20° to 40° C., and most preferably 25° to 37° C., for a period of up to about 5 minutes, to facilitate color development. By incubation, it is meant that the reagents are maintained in contact with each other for the prescribed time interval at the desired temperature before or while color measurements are taken.

In a preferred embodiment, random bias can be avoided by the addition of citrate (or citric acid) to the assay composition described above or to the sample to be assayed. In either case, the citrate (or citric acid) is present in amounts ranging from 1 to 200 mM, preferably 10 to 100 mM. In a preferred embodiment, the assay is conducted using a thin-film element as described above, where the element contains citrate or citric acid in one or more layers of the assay element having a coated range of citrate or citric acid equivalent to 0.1 to 20 mmol/m$^2$. A more preferred range is 1 to 10 mmol/m$^2$. Preferably, the citrate or citric acid is incorporated into the spreading layer during the coating process. Incorporation of the citrate or citric acid into the assays using the chromoionophore compounds of the present invention improves the random bias. Advantage can be taken of the extended dynamic range of the chromoionophores and the ability to obtain calorimetric measurements near or above 600 nm.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

7,16-Bis[2-hydroxy-5-(4-nitro-2-trifluoromethylphenylazo)benzyl]-7, 16-diazo-1,4, 10,13-tetraoxacyclooctadecane Part A. Preparation of 7,16-Bis(2-hydroxybenzyl)-7,16-diazo-1,4,10,13-tetraoxacyclooctadecane 7,16-Diazo-1,4,10,13-tetraoxacyclooctadecane (13 g., 0.05 mole) was added to acetonitrile (150 ml) along with 2-acetoxybenzyl bromide (0.12 mole) and N,N-diisopropyl-N-ethylamine (0.25 mole). The mixture was kept at room temperature for 24 hours, and the solvent was removed until a paste formed. The paste was dissolved in water and the solution extracted twice with methylene dichloride. The extracts were dried to yield 25 g of a thick oil. The oil was dissolved in a mixture of 100 ml of methanol, 10 ml of water, and 1 ml of acetic acid, and the mixture was kept at room temperature for 2 hours. The mixture was chilled, and white crystals formed upon scratching the container with a stirring rod. Diethyl ether was added and the product separated by filtration and dried.

Part B. Preparation of 4-Nitro-2-trifluoromethylphenyldiazonium hexaflourophosphate A solution of sodium nitrite (10 g) in 20 ml water was added to a suspension of 4-Nitro-trifluoromethylaniline (20.6 g) and concentrated hydrochloric acid in ice. When the addition was complete, the mixture was stirred for 1 hour and the treated with 15 ml of 60% hexafluorophosphoric acid producing a solid precipitate. Water was added, the product collected by filtration, the precipitate washed with water, and air dried to yield 27 g (75%)

Part C. Preparation of Title Compound

A solution of 1.5 g of the diazonium compound prepared as described in Part B in 30 ml of ethyl acetate was added with stirring over a 10-minute period to a suspension of 900 mg of the bisphenol prepared in Part A in 75 ml of ethyl acetate. Dye formed immediately, and the mixture was stirred another 10 minutes, then chilled for one hour, the product collected by filtration, washed with diethyl ether, and dried. Yield 1.0 g Elemental Anal. Calc'd (with 2HPF$_6$): C, 40.0; H, 3.7; N, 9.3; F, 28.5; P, 5.2. Found: C, 36.83; H, 3.75; N, 8.47.

EXAMPLE 2

7,16-Bis[2-hydroxy-5-(2-methylsulfonyl-4-nitrophenylazo)benzyl]-7,16-diazo-1,4,10,13-tetraoxacyclooctadecane A solution of 2-methylsulfonyl-4-nitrophenyidiazonium hexafluorophosphate prepared by the procedures of Example 1, Part B, except substituting 2-methylsulfonyl-4-nitroaniline in place of the 4-nitro-2-trifluoromethyaniline (1.7 g, 4.5 mmole) in acetonitrile (50 ml) was added slowly over a 15-minute period to 7,16-bis(2-hydroxybenzyl)-7,16-diazo-1,4,10,13-tetraoxacyclooctadecane prepared as described in Example 1, Part A (1.0 g, 2.11 mmole) in 100 ml of acetonitrile cooled to 0° C. for 3 hours and the solvent removed by evaporation. The residue was washed with water and dissolved by warming in a mixture of methanol and dilute aqueous sodium hydroxide solution. The mixture was cooled, and the product was precipitated by addition of acetic acid, collected by filtration, washed with isopropyl alcohol, then with ether. A small portion was dissolved in N,N-dimethylformamide, precipitated by addition of ethanol, air dried, then further dried for 10 minutes at 90° C., and tested.

EXAMPLE 3

Dry Assay for Calcium Ions

An analytical element of the present invention was prepared in the following format and cut and mounted as slides for calcium assays.

| |
| --- |
| Spreading Layer |
| Sub-Layer |
| Gelatin/Buffer Layer |
| Reagent Layer |
| Support |

To prepare the analytical element of the above format, a dye dispersion of 1% chromoionophore from Example 1, 5% tricresyl phosphate coupler solvent, 0.6% Alkanol XC sodium alkyl napthalene sulfonate surfactant, and 6% gelatin was prepared by standard photographic coupler dispersion methods involving milling of the dye, solvent, and surfactants to a uniform, stable dispersion of desired particle size.

This dye dispersion was then coated on a poly(ethylene terephthalate) support, with the following layer composition:

Reagent Layer 1

0.25 g/m$^2$ of dye as a dispersion, 10.0 g/m$^2$ gelatin, and 0.025 mol/m$^2$ TRIS buffer (2-amino-2-(hydroxymethyl)-1, 3-propanediol buffer, preset for pH 7.7 at 37° C.).

Gelatin/Buffer Layer 2

0.035 mol/m² TRIS (preset mix for pH 7.7 at 37° C.) in 10.0 g/m² gelatin, crosslinked with 0.5 g/m² bis(vinylsulfonylmethyl) ether.

Sub Layer 3

0.39 g/m² poly(N-isopropylacrylamide).

Spreading Layer 4

TiO₂ spread layer having the following composition:

67.2 g/m² titanium dioxide 9.8 g/m² cellulose acetate 1.8 g/m² Triton X-405 (octylphenoxy polyethoxy ethanol nonionic surfactant)

0.9 g/m² Brij 78 (polyoxyethylene (20) stearyl ether, nonionic surfactant) 1.8 g/m² Estane 5715, a polurethane elastomer sold by B. F. Goodrich.

This element was used to determine calcium concentration in 50 patient sera ranging in calcium concentration from 1.57 to 16.5 mg/dL, 3 replicates per serum sample. The reflection density resulting from complexation of the calcium ions with the chromoionophore compounds of the present invention was read at 600 nm using a commercially available Johnson & Johnson VITROS slide analyzer. The calcium levels determined experimentally with the above analytical element correlated with those determined on the same sera samples using commercially available calcium analytical elements.

EXAMPLE 4

Dry Assay for Calcium Ions

Figure 2:
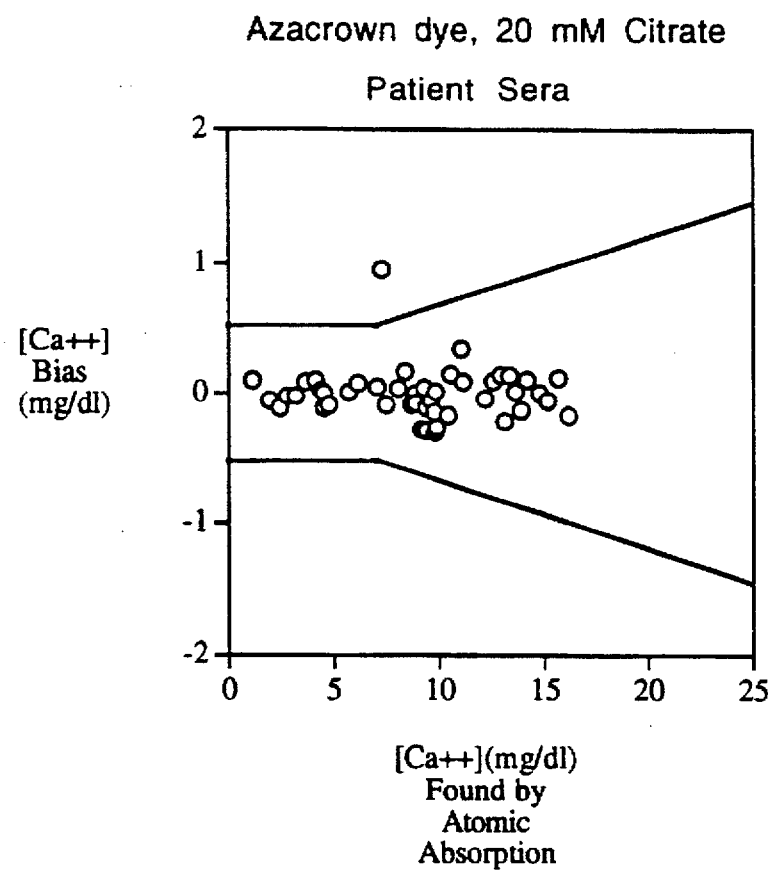
FIG. 2 is a graph of the calcium levels measured in serum samples using the analytical elements of the present invention with added citrate and showing the bias from the predicted calcium levels.

An analytical element of the present invention was prepared in the format of Example 3 with and without citric acid added to the TiO₂ spread layer at a concentration level of 2.0 mmol/m². These coatings were used to analyze 50 patient serum samples for calcium level, with the developed dye reflection densities read at a wavelength of 600 nm. The reference values (determined by atomic absorption spectroscopy) for the serum were used to calibrate each coating; then the calcium level for each serum was predicted from the corresponding calibration curve. The bias was calculated as the difference between the value predicted by the coating and the reference value. The residual sum of squares was calculated using the formula:

Residual Sum of Squares=Σ(predicted concentration—reference concentration)² to give 4.07 (no citrate) and 1.69 (plus citrate). The individual sample bias is shown plotted in FIG. 1 (no citrate) and FIG. 2 (plus citrate). Clearly the elements containing the citric acid in the spread layer exhibited significantly less bias than the corresponding elements without citric acid.

The invention has been described in detail with particular reference to preferred embodiments thereof, but it will be understood that variations and modifications can be effected within the spirit and scope of the invention.

We claim:

1. A compound of Formula I:

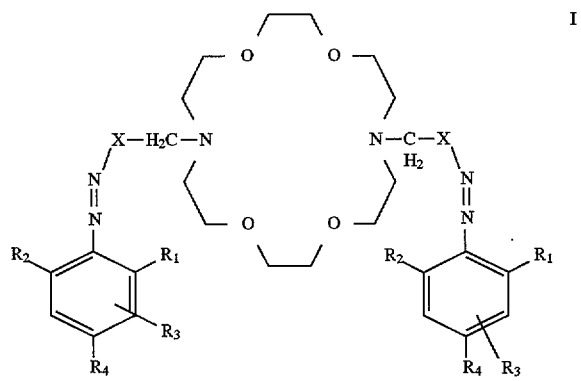

wherein X is a phenol, naphthol or quinolinol moiety selected from those of the formulae:

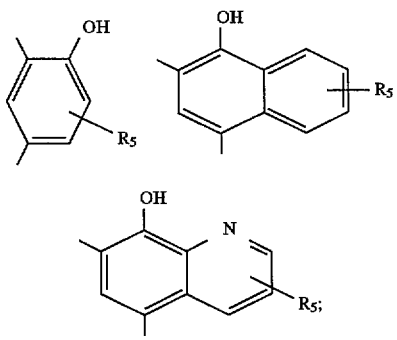

$R_1$, $R_2$, $R_3$, $R_4$ and $R_5$ are independently selected from hydrogen, halo, cyano, nitro, ($C_1$–$C_6$) alkyl, ($C_2$–$C_8$) acyl, acetamido, mercapto, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, and trifluoromethyl; provided that when X is phenol, at least one of $R_1$ and $R_2$ is an electron withdrawing group selected from halo, cyano, nitro, acyl of 2 to 8 carbon atoms, mercapto, and triflouromethyl, and provided that when X is phenol and $R_5$ is hydrogen, $R_1$ or $R_2$ in combination with $R_4$ are not both nitro;

wherein said compound of Formula I has absorption at a wavelength greater than about 580 nm when complexed with calcium ion, and is soluble in organic coupler solvents.

2. The compound of claim 1 wherein X is phenol, $R_4$ is nitro and $R_5$ is hydrogen.

3. The compound of claim 1 wherein X is phenol, $R_4$ is nitro, $R_5$ is hydrogen and $R_3$ is a ($C_1$–$C_6$) alkyl group, provided that when one of $R_1$ or $R_2$ is trifluoromethyl and the other is hydrogen, $R_3$ may also be hydrogen.

4. The compound of claim 1 wherein X is phenol, $R_1$ is trifluoromethyl; $R_2$, $R_3$ and $R_5$ are hydrogen and $R_4$ is nitro.

5. An aqueous composition buffered to a pH of from about 6 to about 9 containing a compound of claim 1.

6. An analytical element for the determination of calcium ions comprising an absorbent carrier material containing a compound of the formula I:

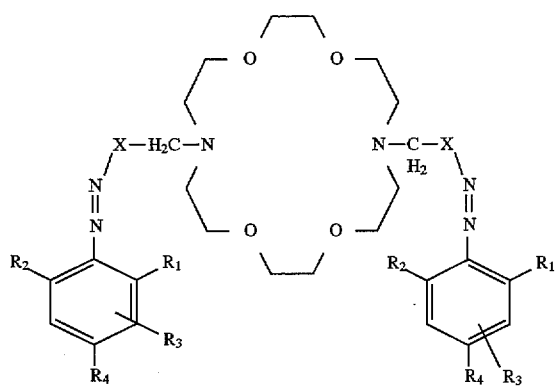

wherein X is a phenol, naphthol or quinolinol moiety selected from those of the formulae:

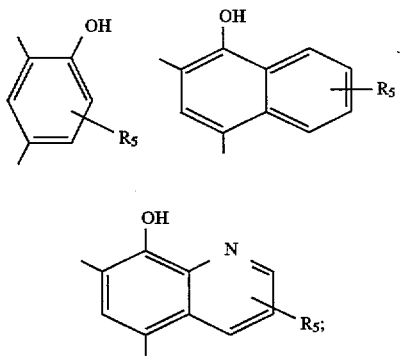

$R_1$, $R_2$, $R_3$, $R_4$ and $R_5$ are independently selected from hydrogen, halo, cyano, nitro, ($C_1$–$C_6$) alkyl, ($C_2$–$C_8$) acyl, acetamido, mercapto, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, and trifluoromethyl; provided that when X is phenol, at least one of $R_1$ and $R_2$ is an electron withdrawing group selected from halo, cyano, nitro, acyl of 2 to 8 carbon atoms, mercapto, and triflouromethyl, and provided that when X is phenol and $R_5$ is hydrogen, $R_1$ or $R_2$ in combination with $R_4$ are not both nitro;

wherein said compound of Formula I has absorption at a wavelength greater than about 580 nm when completed with calcium ion, and is soluble in organic coupler solvents.

7. An analytical element for the determination of calcium ions comprising a nonporous support having thereon a reagent zone and a porous spreading zone, said element containing in at least one of said zones a compound of formula I:

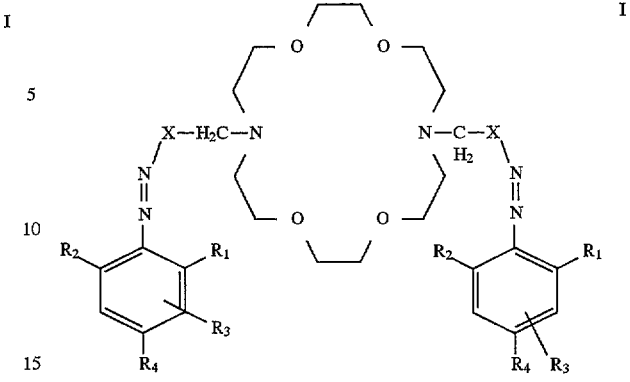

wherein X is a phenol, naphthol or quinolinol moiety selected from those of the formulae:

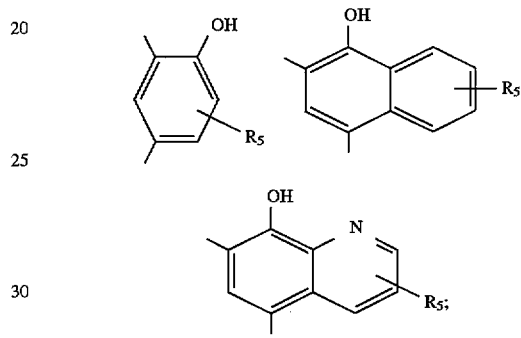

$R_1$, $R_2$, $R_3$, $R_4$ and $R_5$ are independently selected from hydrogen, halo, cyano, nitro, ($C_1$–$C_6$) alkyl, ($C_2$–$C_8$) acyl, acetamido, mercapto, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, and trifluoromethyl; provided that when X is phenol, at least one of $R_1$ and $R_2$ is an electron withdrawing group selected from halo, cyano, nitro, acyl of 2 to 8 carbon atoms, mercapto, and triflouromethyl, and provided that when X is phenol and $R_5$ is hydrogen, $R_1$ or $R_2$ in combination with $R_4$ are not both nitro;

wherein said compound of Formula I has absorption at a wavelength greater than about 580 nm when complexed with calcium ion, and is soluble in organic coupler solvents.

8. The element of claim 7 wherein said zones are superposed layers.

9. The element of claim 7 wherein said compound of formula I is in said reagent zone.

10. The element of claim 7 additionally containing 1 to 200 mM of citrate or citric acid.

11. The element of claim 10 wherein the citrate or citric acid is contained in the spreading zone at a concentration of 0.1 to 20 mmol/m².

12. A method for quantitative determination of calcium ions which comprises:

(a) contacting a liquid sample suspected of containing calcium ions with a chromoionophore compound of the formula:

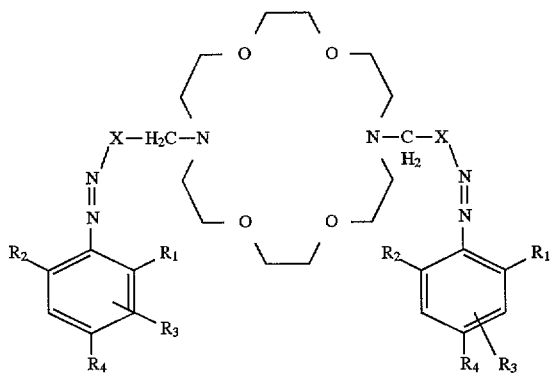

wherein X is a phenol, naphthol or quinolinol moiety selected from those of the formulae:

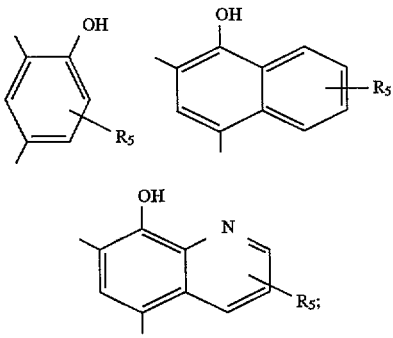

$R_1$, $R_2$, $R_3$, $R_4$ and $R_5$ are independently selected from hydrogen, halo, cyano, nitro, ($C_1$–$C_6$) alkyl, ($C_2$–$C_8$) acyl, acetamido, mercapto, trifluoromethyl, aryl, and substituted aryl wherein the aryl moiety is selected from phenyl and naphthyl and the aryl substituent is selected from halo, cyano, nitro, ($C_1$–$C_6$) alkyl, ($C_2$–$C_8$) acyl, phenyl, acetamido, mercapto, and trifluoromethyl; provided that when X is phenol, at least one of $R_1$ and $R_2$ is an electron withdrawing group selected from halo, cyano, nitro, acyl of 2 to 8 carbon atoms, mercapto, and triflouromethyl, and provided that when X is phenol and $R_5$ is hydrogen, $R_1$ or $R_2$ in combination with $R_4$ are not both nitro;

wherein said compound of Formula I has absorption at a wavelength greater than about 580 nm when complexed with calcium ion, and is soluble in organic coupler solvents; and (b) determining colorimetrically the quantitative presence of calcium in the sample by measuring the optical density change resulting from the complexation of calcium ions with the compound of formula I.

13. The method of claim 12 wherein the chromoionophore compound is contained in a dry analytical element for the determination of calcium ions comprising a nonporous support having thereon a reagent zone and a porous spreading zone.

14. The method of claim 13 wherein the spreading zone contains 0.1 to 20 mmol/m² citrate or citric acid.

* * * * *